Figure 2:
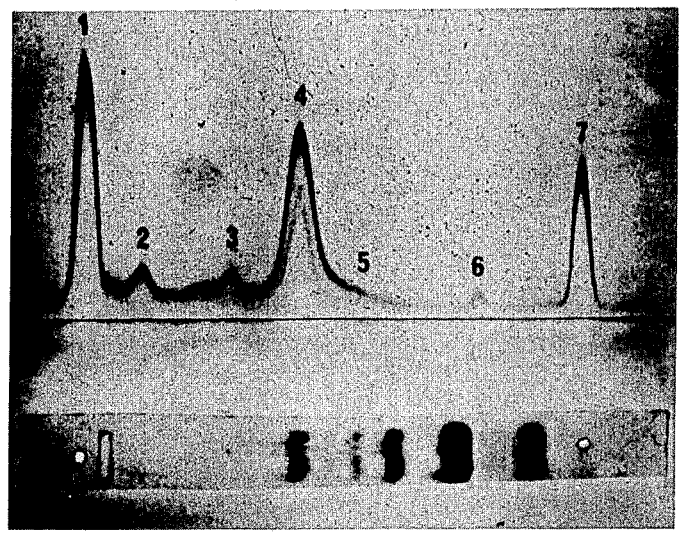

United States Patent [19]

Shainoff

[11] 4,275,196
[45] Jun. 23, 1981

[54] GLYOXAL AGAROSE

[75] Inventor: John R. Shainoff, Cleveland Heights, Ohio

[73] Assignee: The Cleveland Clinic Foundation, Cleveland, Ohio

[21] Appl. No.: 23,179

[22] Filed: Mar. 23, 1979

[51] Int. Cl.³ .................. B01D 57/02; B01J 13/00; C07H 15/00
[52] U.S. Cl. .................. 536/115; 530/120; 530/116; 204/180 G; 252/316
[58] Field of Search .......... 204/180 G, 299; 536/4, 536/6, 115, 120, 116; 424/2, 12

[56] References Cited

U.S. PATENT DOCUMENTS

| | | | |
|---|---|---|---|
| 3,085,085 | 4/1963 | Wismer et al. | 536/120 |
| 3,497,437 | 2/1970 | Louderback et al. | 204/180 G |
| 3,527,712 | 9/1970 | Renn et al. | 204/180 G X |
| 3,640,809 | 2/1972 | Polson et al. | 204/180 G |
| 3,873,514 | 3/1975 | Chu et al. | 204/180 G X |
| 4,098,615 | 7/1978 | Cummisford et al. | 536/2 |

OTHER PUBLICATIONS

Rose, "The Condensed Chemical Dictionary", 7th Ed., pp. 24, 454, 456 (1968).
Grant, "Hackh's Chemical Dictionary", 4th Ed., (1969) p. 19.

Primary Examiner—Howard S. Williams
Attorney, Agent, or Firm—Fay & Sharpe

[57] ABSTRACT

A new composition of matter is provided having novel, valuable attributes in the zonal immobilization of proteins of biochemical origin which expands man's capacity to separate, isolate, detect, and sequentially sorb and desorb, concentrate, and quantify and qualify picomole size samples or specimens of complex proteins of biochemical origin into fundamentally interesting fractions for studies to expand the understanding of, illustratively, the complex proteins in lesions of atherosclerosis, antigens, antibodies, enzyme immobilization in studies of enzymatic actions in body tissues and functions, immunoglobulins, genetic aberrations, molecular size separations of complex proteins, and extends the sensitivity of detection of such isolates beyond that achievable by prior art radio immunoassay techniques.

3 Claims, 4 Drawing Figures

FIG. 1

STEP 1.
ANTIGEN SEPARATION AND IMMOBILIZATION

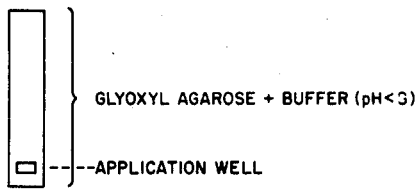
GLYOXYL AGAROSE + BUFFER (pH<3)
APPLICATION WELL

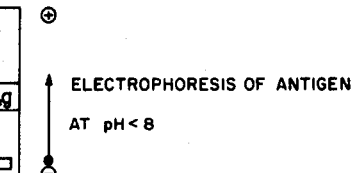
ELECTROPHORESIS OF ANTIGEN AT pH<8

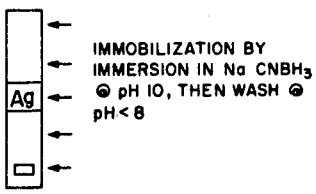
IMMOBILIZATION BY IMMERSION IN Na CNBH$_3$ @ pH 10, THEN WASH @ pH<8

STEP 2.
ANTIBODY ABSORPTION

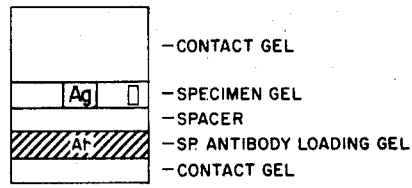
—CONTACT GEL
—SPECIMEN GEL
—SPACER
—SP. ANTIBODY LOADING GEL
—CONTACT GEL

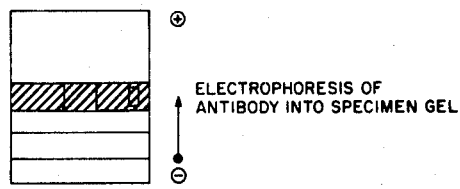
ELECTROPHORESIS OF ANTIBODY INTO SPECIMEN GEL

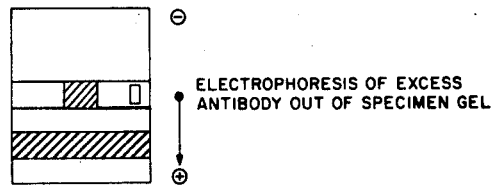
ELECTROPHORESIS OF EXCESS ANTIBODY OUT OF SPECIMEN GEL

STEP 3.
DESORPTION OF ANTIBODY

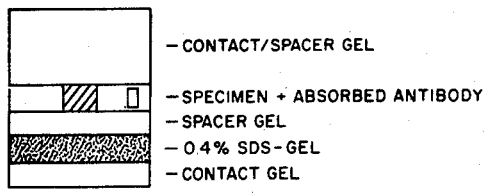
—CONTACT/SPACER GEL
—SPECIMEN + ABSORBED ANTIBODY
—SPACER GEL
—0.4% SDS-GEL
—CONTACT GEL

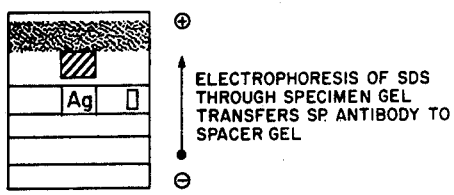
ELECTROPHORESIS OF SDS THROUGH SPECIMEN GEL TRANSFERS SP. ANTIBODY TO SPACER GEL

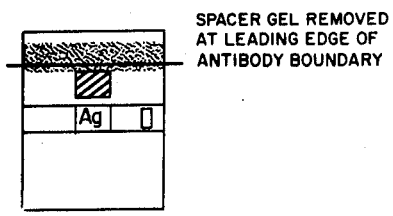
SPACER GEL REMOVED AT LEADING EDGE OF ANTIBODY BOUNDARY

STEP 4.
MEASUREMENT OF DESORBED ANTIBODY

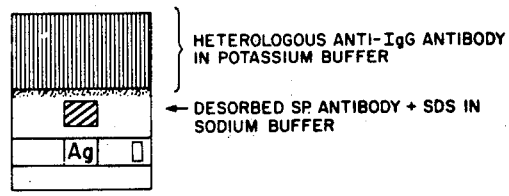
HETEROLOGOUS ANTI-IgG ANTIBODY IN POTASSIUM BUFFER
←DESORBED SP. ANTIBODY + SDS IN SODIUM BUFFER

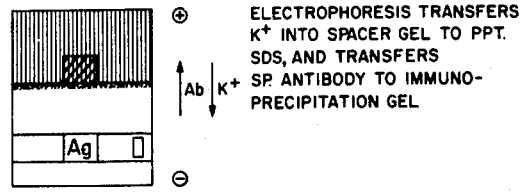
ELECTROPHORESIS TRANSFERS K$^+$ INTO SPACER GEL TO PPT. SDS, AND TRANSFERS SP. ANTIBODY TO IMMUNO-PRECIPITATION GEL

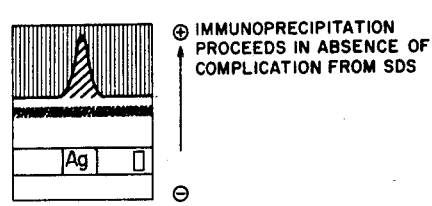
IMMUNOPRECIPITATION PROCEEDS IN ABSENCE OF COMPLICATION FROM SDS

STEP 1

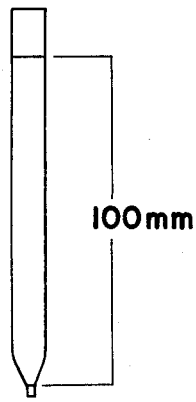

2 ml OF 2% GLYOXYL AGAROSE EQUILIBRATED WITH RABBIT FIBRINOGEN (1mg/ml) IN NaCl-PO$_4$ BUFFER, pH 7.4

100mm

STEP 2

APPLY 50 λ SAMPLE AND FOLLOW WITH 0.4 ml FIBRINOGEN BUFFER SOLUTION

STEP 3

MAKE ALKALINE BY ELECTROPHORESIS TO ADSORB PROTEIN ONTO GLYOXYL AGAROSE

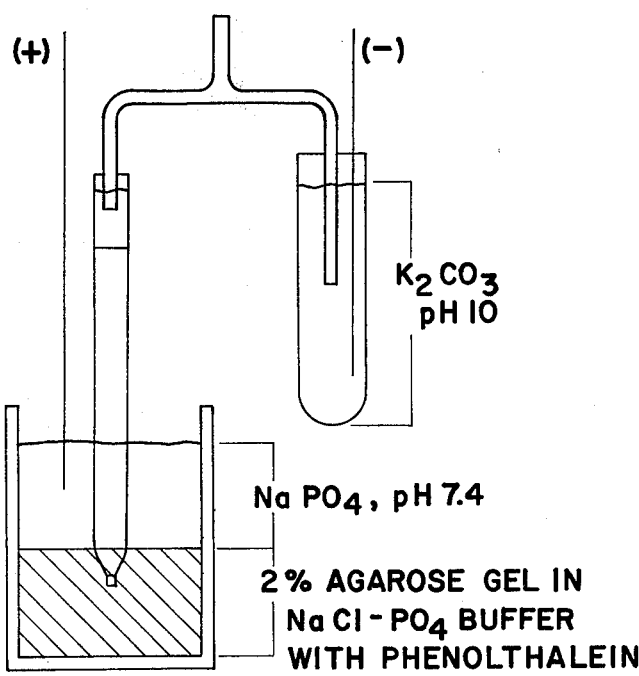

(+)   (−)

K$_2$CO$_3$ pH 10

Na PO$_4$, pH 7.4

2% AGAROSE GEL IN NaCl-PO$_4$ BUFFER WITH PHENOLTHALEIN

STEP 4

PERMANENTLY IMMOBILIZE PROTEIN BY WASHING WITH 2ml 0.1M NaHCO$_3$ BUFFER + 0.02M NaCNBH$_3$, pH 10 AFTER 15 MIN WASH WITH NaCl-PO$_4$ BUFFER TO NEUTRALIZE

STEP 5

APPLY 50 λ FLUORESCEINATED ANTIBODY AND WASH WITH 4ml NaCl-PO$_4$ BUFFER

FIG. 3

GLYOXAL AGAROSE

BACKGROUND OF THE INVENTION

The concept of immobilizing protein fragments and complexes including as illustrative antigens, antibodies, enzymes, etc., on gel structures has been described in the art. Gels are also widely used as support matrices for separating proteins by electrophoresis. However, no single gel developed heretofore could be used for both separating and immobilizing proteins. Ability to do either or both on one gel would provide options heretofore unavailable for design of new analytical methods. The gel substrates heretofore available and known have been too unstable, too reactive or of insufficient binding quality to be used for both separating and immobilizing proteins. Further, gels to be useful for electrophoretic separations in the studies within the scope of the field of use here of interest should be repeatably meltable, in the first instance to permit casting into slabs or sheets of a configuration useful for the specific electrophoretic separation contemplated, for example cross electrophoresis. Several known modifications of agarose commonly used for preparing affinity absorbents, were reproduced and their quality explored in an attempt to find one gel suitable for the contemplated electrophoretic procedures. All protein immobilizing gels tested were found to lose their activity and become resistant to melting due to cross-linking and consequent decomposition at melting temperatures. By exception, Parikh et al., *Methods in Enzymology* 34: 77–102 (1974) prepared for protein immobilization an aldehyde derivative of agarose by direct oxidation of agarose with periodate, which by our test was found to withstand melting. However, the binding capacity was objectionably low because of the small number of vicinal hydroxyl groups subject to partial oxidation.

The aldehyde rich glyoxal agarose of the present invention has excellent binding capacity and can be melted into sheets or slabs for multiple electrophoresis separations without complication. The aldehyde groups are essentially inert towards protein at neutral or acidic pH, but rapidly react with protein amino groups to form Schiff-base linkages. The inertness enables it to be used as a gel support for separating protein without binding at neutral pH, and high reactivity enables it to bind and immobilize the separated proteins simply through change to alkaline pH. The strong binding at alkaline pH can be reversed by neutralization, or it can be made irreversible by adding either by electrophoresing into the gel or immersing the cyanoborobydride gel in buffer with it. At pH near 10 the binding capacity is quite high—of the order of 2 to 3 mg of protein per mg of glyoxal agarose, as measured with both fibrinogen and cytochrome C, two proteins of widely differing molecular weight.

Thus it can be seen that the novel glyoxal agarose of this invention will have many and varied applications in immunochemical, enzymological and biochemical analysis and research to provide means for carrying out critical separations and analyses of complex biological specimens by solid phase methods. Mixtures of closely related substances may be separated on the gel, may be eluted or concentrated, or they may be permanently attached to the gel matrix to thereby facilitate identification of the substances and their possible relationships to other identified substances in the mixture upon analysis.

A principal purpose of the invention is to provide a gel complex which is of such nature as to controllably bind specific proteins either reversibly, irreversibly, or not at all as may be selected by an investigator.

A first function is to selectively bind a desired protein to concentrate the selected protein from a dilute aqueous medium. This can be accomplished reversibly. That is, the protein may be recovered from the gel after its selective sorption, or it may be irreversibly bound to the gel, or it may so processed that a given protein is not bound at all to the novel gel of this invention. It is considered that the gel has the capacity to bind proteins through formation of Schiff base linkages—which base linkages are non-dissociable at alkaline pH of greater than about 9.5, but which bases are readily dissociated at neutral and acid pH. The inertness of the gel at neutral or acidic pH makes possible separation of protein from complex mixtures of them in positions and according to molecular weight range by either electrophoresis or by gel filtration. Once separated, the protein can be attached to the gel by making the solution alkaline, and the attachment made permanent by treating with cyanoborohydride. By controlled means it becomes feasible to sequentially sorb, desorb, mobilize and demobilize protein within a relatively narrow molecular weight range—repeated experiments providing reproducible profiles of their molecular weights and electrophoretic mobility, even when working with picomole size samples, $1 \times 10^{-12}$.

Once having separated the specific proteins of interest (illustratively) antigens and antibodies) detection, identification and assay of the isolate can be carried forward by known techniques.

The invention disclosed herein has been reduced to practice in detecting fibrinogen related antigens which have been heretofor non-specifically precipitated and most often denatured by the variable prior art means employed for their recovery. The sensitivity of the method of zonal immobilization of proteins permits detection and measurement of specific antigenic determinants in a 0.02 mg tissue specimen (microtome section 1 $cm^2 \times 2$ micron), where the specific antigenic determinant is that portion of the antigen molecule that determines the specificity of the antigen-antibody reaction.

Complex separations are potential through electrophoresis to produce a separated protein-gel fraction. This fraction may be immobilized (temporary) by a pH shift to a pH 10 with carbonates, or permanently by a second electrophoresis which provides intimate contact of the protein-gel fraction with a small amount of a reducing agent, preferably a cyanoborohydride ion. The Schiff base linkages are converted to stable alkyl amino linkages. The technique permits detection and assay of specific protein antigens thus separated.

The novel gel of this invention makes possible capture and separation by, if desired, repeated sequential sorption, desorbtion, mobilizing and immobilizing biologically germane protein bodies within very narrow ranges of molecular weight and to do so repetitively with reproducible results employing specimen samples of quantities in the picomole levels. The following examples are illustrative:

EXAMPLE 1

The product of this invention, herein referred to as glyoxal agarose (but which is also identified by the invention as glyoxyl agarose) is produced from an aqueous suspension of commercial 4% agarose gel of 50–100 mesh in distilled water after carefully washing with water. A 200 ml suspension containing 2 grams of agarose gel of commercial quality as above is treated with 20 ml of glycidol and 100 ml of 1 M NaOH containing NaBH$_4$ (2 mg/ml) as an antioxidant. The aqueous suspension (320 ml) was gently stirred by rocking for 18 hours at 25° C. The reaction product was repeatedly washed with distilled water through a Buchner funnel until alkalinity of the effluent was reduced to pH 7±0.5. The resultant glycerated agarose occupied a bed volume of 170±10 ml which physically resembled the original suspended agarose.

The washed glycerated agarose was re-suspended in sufficient distilled water to give a volume of 250 ml., admixed with 70 ml. of 0.16 M NaIO$_4$ and gently rocked for one hour at room temperature.

The final product was again water washed to remove by-product formaldehyde present along with other possible contaminants from the reaction. Thiosulfate titration of samples periodically removed during periodate oxidation of the glyceral residues indicated the reaction was completed within 15 minutes. Total periodate consumption corresponded to 0.06 mmoles per ml of bed volume of the gel or 1.6 mmoles of aldehyde groups per gram (dry weight) of agarose. Further analyses indicated approximately one glyoxal residue per one and one third biose units in the novel glyoxal agarose product. Control tests employing cytochrome C, albumin, fibrinogen and gammaglobulin confirmed a protein binding capacity of between 2 and 4 mg protein per mg. of the glyoxal agarose at pH above about 9.5.

EXAMPLE 2

A novel electroimmuno assay method has been made possible through use of the glyoxal agarose medium. One sequentially sorbs, desorbs and cascades antibodies in the glyoxal agarose medium which is controlled to bind protein either reversibly or irreversibly, or optionally not at all. Proteins, illustratively, are separated on the gel as with ordinary unaltered agarose at neutral or acid pH. The separated proteins may be temporarily immobilized in zones in the gel with alkaline buffers above a pH of about 9.5 or they can be permanently bound in tight zones with alkaline buffer containing sodium cyanoborohydride. Analytical determinations by detection and assay of specified antigens can be made on the immobilized proteins.

This procedure involves an indirect cascaded antibody technique which involves electrophoresis through the gel of fluoresceinated antibody IgG. The absorption of the antibody is measured by desorption of the antigen and its subsequent immuno precipitation with anti-IgG antibodies. Desorption of the antigen is accomplished by electrophoresing sodium dodecylsulfate into the glyoxal agarose gel, and transferring the IgG through another gel which contains potassium ions which removes the sodium dodecylsulfate by precipitation in the second gel. The process is further cascaded by fixing the desorbed IgG in the immobilizing glyoxal agarose gel which again serves as an antigen to bind additional antibody protein.

The procedure of Example 2 is illustrated schematically in FIG. 1, and the results of the analysis are shown in FIG. 2.

The following detailed discussion is an explanation of the steps illustrated in FIG. 1, as these steps apply to the results shown in FIG. 2.

Step 1. Sample Gel

A mixture of plasma proteins consisting of 0.4 μg of human fibrinogen, 4.0 μg of bovine serum albumin, and 4.0 μg of cytochrome C were separated by electrophoresis in 0.02 M sodium phosphate containing 0.1% (sodium dodecylsulfate) SDA and were subsequently immobilized by immersion of the gel in 0.04 M sodium carbonate containing 0.01 M NaCNBH$_3$ and 1% Lubrol ®. This procedure attached the protein to the sample gel at positions indicative of their molecular size. The selection of proteins used in the illustration was made to demonstrate the separation according to size. After preparation of the sample gel, it was washed with 0.02 M sodium phosphate at pH 6.9 to prepare it for exposure to anti-fibrinogen antibodies.

Step 2. Exposure to Anti-Fibrinogen Antibodies

A 0.6 cm wide strip of 1% agarose gel containing fluoresceinated rabbit anti-human fibrinogen antibodies was cast at a position 0.3 cm to the cathodal side of the sample gel, and the antibody protein was electrophoresed anodally into the sample gel. After 3 hours, the antibody was electrophoresed back out of the sample gel by reversing the current. Inspection with a UV-light showed that the fibrinogen in the sample gel retained the antibody, while little or none was held in other regions of the gel.

Step 3. Desorption and Measurement of the Specifically Absorbed Antibody

This step involved dissociating the antibody from the fibrinogen with SDS, and electrophoresing the antibody through a spacer gel with potassium phosphate to precipitate the detergent, and continuing the electrophoresis of the antibody into gel containing swine anti-rabbit IgG for measurement of the antibody. A 0.6 cm wide strip of gel containing 0.18% SDS was cast at the cathodal side of the sample gel, and current was applied at 2 V/cm until the SDS migrated to a distance 1 cm ahead of the anodal edge of the sample gel so as to place the desorbed antibody 0.5 cm ahead of the sample gel. (Migration of the SDS was easily followed by placing 1 μl of cytochrome C in a well at the edge of the sample gel, because the cytochrome C did not migrate in absence of SDS but after convergence with SDS migrated at the front of the detergent boundary). The gel in front of the eluted antibody was then removed, and was replaced with gel containing swine anti-rabbit IgG antibodies in 0.02 M potassium phosphate buffer at pH 6.9. Upon resuming electrophoresis, cathodal migration of the potassium caused the SDS to precipitate completely without discernible entry into the newly cast gel, while the fluoresceinated rabbit IgG with negative charge imposed by the fluorescein migrated anodally to form the "rocket" precipitin pattern through reaction with the swine-anti-rabbit IgG antibody in the gel. Comparison of the size of the precipitin rockets formed by the desorbed fluoresceinated anti-fibrinogen antibody with those formed by known amounts applied as a reference provided a means of measuring the amount of antibody that had been specifically bound by the fibrinogen. The amounts of the various fibrinogen related antigens and their molecular sizes indicated the area and position (resp.) of the rockets are tabulated in Table 1.

TABLE 1

| Curve Number | U.A.-Identification | Fibrinogen Equivalent | mg/ml |
|---|---|---|---|
| Sample size (0.2 ml, 2 μl of 1/10 dilution. | | | |
| 1. (calibration) | 0.25 Mg. Rabbit IgG | 0.32 | Calib. |
| 2. | $10^7$ (Fibrinogen-Fibrin-Polymer) | 0.33 | 0.16 |
| 3. | 700,000 (Fibrinogen dimer) | 0.036 | 0.18 |
| 4. | 340,000 (Fibrinogen dimer) | 0.35 | 1.75 |
| 5. | 280,000 (Fragment X) | 0.027 | 0.14 |
| 6. | 40,000 to 30,000 (Fragment A, B or C) | 0.006 | 0.03 |
| 7. (calibration) | 0.5 Mg rabbit IgG | 0.16 | calib. |

EXAMPLE 3

A second method for attaching a separated protein to the novel gel of this invention has been demonstrated. In this method the conventional gel filtration methods for detection of fibrin complexes by plural fraction collection and multiple analyses of the eluted protein to characterize the chromotograph is superseded.

The proteins are separated by filtration through the glyoxal agarose gel of this invention separating them into displaced positions in the gel. Subsequently, the separated displaced proteins in the gel are immobilized into tight zones by electrophoresing alkaline cyanoborohydride into the suspending gel medium. Use of small disposible columns (Pasteur pipettes) for this zonal immobilization is advantageous. Thereafter, the immobilized zonal fractions are stained. A fluorescent or radio iodinated anti-human fibrinogen antibody is useful as the staining medium.

The procedural steps of Example 3 are illustrated in FIG. 3. An analysis is depicted based on the procedure in FIG. 4.

Referring specifically to FIG. 2 the following description is pertinent:

Cascade immunoelectrophoretic analysis of the molecular weight distribution of fibrinogen related antigens in the plasma fibrinogen sample. The plasma proteins together with a fluorescent labelled ribonuclease marker were separated by electrophoresis and subsequently immobilized in the sample gel. Carbamylated anti-fibrinogen antibody was electrophoresed into the sample gel and then removed by reversing current. Antibody that was retained by the immobilized fibrinogen antigens in the gel was then desorbed by electrophoresing sodium dodecyl sulfate into the gel and through a spacer gel in which the SDS was removed by precipitation with potassium ion. On continuing electrophoresis, the anti-fibrinogen antibody migrated through the spacer without interference from SDS, and into a gel containing anti IgG antibodies for measurement of the anti-fibrinogen. The areas under the rockets formed by the IgG-anti IgG precipitate measures the amount of the variant forms of fibrinogen antigens in the sample gel. The quantities of antigens are expressed on the basis that 1 μg of fibrinogen absorbs 1.6 μg of anti-fibrinogen antibody. Peaks 1 and 7 in the illustration are from known amounts of anti-fibrinogen antibody applied as calibration standards. The molecular weight, concentrations, and probable nature of the fibrinogen derivatives in the sample are tabulated on page 10.

Figure 4:
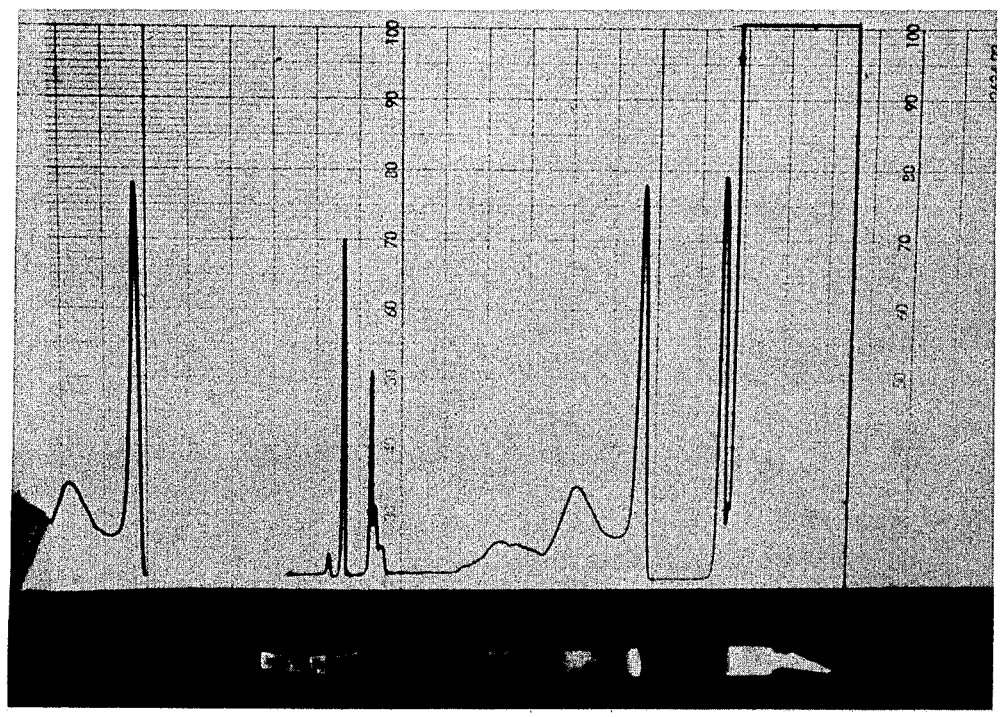

Referring specifically to FIG. 4, fibrin complexes and fibrinogen in a human plasma sample were separated on a column of 4% glyoxyl agarose equilibrated with rabbit fibrinogen. The protein was then immobilized, and the distribution of fibrinogen related antigens was established with fluoresceinated anti-human fibrinogen antibody.

As used herein the term glyoxal agarose is equivalent to the term glyoxyl agarose.

Having thus described the best mode presently known to me to prepare the novel gel of this invention and illustrated novel methods for its usefulness in the arts, what I claim is:

1. Glyoxal agarose.
2. Glyoxal agarose wherein the agarose molecule contains not less than 0.5 nor more than two functional units per biose unit of agarose.
3. Glyoxal agarose having a protein binding capacity under alkaline conditions of not less than about 2 and not more than about 4 mg. protein per mg. of the agarose compound.

* * * * *